United States Patent [19]

Yamagiwa

[11] 4,444,222

[45] Apr. 24, 1984

[54] AUTOMATIC LIQUID-SUPPLY STOPPER PLUG

[75] Inventor: Tamio Yamagiwa, Tokyo, Japan

[73] Assignee: Hi-Sonic Co., Ltd., Tokyo, Japan

[21] Appl. No.: 377,610

[22] Filed: May 13, 1982

[30] Foreign Application Priority Data

May 18, 1981 [JP] Japan .................. 56-74361

[51] Int. Cl.³ .................................. F16K 21/18
[52] U.S. Cl. .................. 137/393; 137/625.38; 141/198; 222/64
[58] Field of Search .............. 222/64, 65, 55, 56; 251/DIG. 1; 137/625.33, 625.38, 625.37, 624.27, 386, 393; 141/192, 198

[56] References Cited

U.S. PATENT DOCUMENTS

| 3,631,891 | 1/1972 | Brumm | 137/625.38 |
| 4,191,208 | 3/1980 | Mylander | 137/393 |

FOREIGN PATENT DOCUMENTS 34-10876 12/1959 Japan .

Primary Examiner—Joseph J. Rolla
Assistant Examiner—Kenneth Noland
Attorney, Agent, or Firm—Brumbaugh, Graves, Donohue & Raymond

[57] ABSTRACT

An automatic liquid-supply stopper plug has a casing body which has an inlet port and a discharge port. Within the casing body, an inverted cup shaped member and a valve seat member are provided to be opposed to each other. A movable valve member is positioned so that it can slide on the inverted cup shaped member and the valve seat member to open or close a passage of liquid through the valve seat member. A first conduit which communicates with the discharge port is provided for pushing the movable member upwardly. A second conduit which communicates with the discharge port is provided for pushing the movable valve member downwardly when a preset level of liquid is obtained to stop the liquid-supply.

15 Claims, 1 Drawing Figure

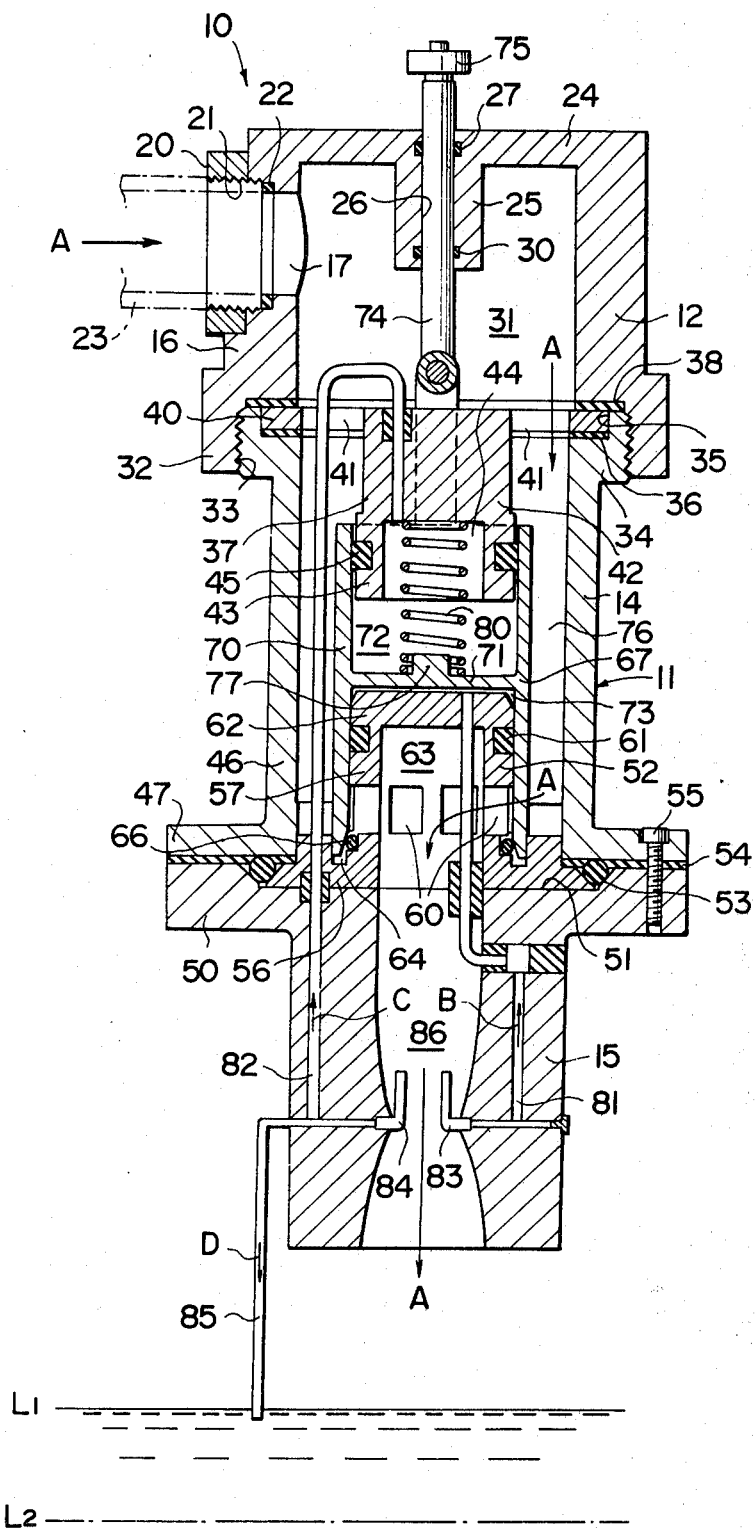

AUTOMATIC LIQUID-SUPPLY STOPPER PLUG

BACKGROUND OF THE INVENTION

1. Field of the Invention

The present invention relates to an automatic liquid-supply stopper plug, and more particularly to a plug for stopping liquid supply automatically when the level of the liquid arrives at a preset level.

2. Description of the Prior Art

The automatic liquid-supply stopper plug of the conventional type has a valve which is closed instantaneously to stop liquid supply when the liquid level arrives at a preset level. As a result, the pressure in the piping at the liquid feed side is abruptly changed due to water-hammering, leading to generation of striking harsh sound or leading to breakdown of liquid feed piping or damage of the automatic water-supply stopper plug per se at the worst.

In order to abate the water-hammering action, it has been proposed to provide an air chamber at the liquid feed side of the automatic water-supply stopper plug to absorb the hammering action. However, provision of such an air chamber is accompanied with disadvantageous increase in production cost. Particularly, when the plug is incorporated in a large-scale liquid supply system through which a large amount of liquid is fed at a high rate, an air chamber having an extremely large capacity must be provided, which results in unacceptable increase in cost.

OBJECTS AND SUMMARY OF THE INVENTION

It is, therefore, a primary object of this invention to provide an automatic liquid-supply stopper plug in which a valve member is closed slowly and quietly to avoid the occurrence of water hammering when the supply of liquid in stopped at a preset level of liquid.

Another object of this invention is to provide an automatic liquid-supply stopper plug by which the occurrence of water-hammering can be avoid almost completely even when a large amount of liquid is flowned through the plug at a high rate.

A further object of this invention is to provide an automatic liquid-supply stopper plug having no air-chamber, otherwise required in the conventional plug for absorbing the water-hammering action.

A still further object of this invention is to provide an automatic liquid-supply stopper plug which is inexpensive in production cost and relatively simple in structure.

The automatic liquid-supply stopper plug provided according to this invention comprises, in combination: a casing body having an inlet port at the upper portion thereof and a liquid discharge port at the lower portion thereof; an inverted cup shaped member fixedly received in said casing to be suspended therein; a valve seat member mounted in said casing body at the position below said inverted cup shaped member and having a generally tubular wall extending downward from the top face thereof, said downward-extending wall being provided with at least one window type opening communicating with said liquid discharge port of said casing body; a valve member having a generally tubular wall and a partition wall of disk shape for sealingly and slidably surrounding said inverted cup shaped member and for sealingly and disengageably covering said window type opening of said valve seat member to open or close said opening, said tubular wall and said partition wall defining an upper chamber in combination with said inverted cup shaped member, and said tubular wall and said partition wall defining lower chamber in combination with said valve seat member; a compression spring fitted between the inner face of said inverted cup shaped member and the top face of said valve member for normally depressing said valve member in downward direction; a manually operated knob connected to said valve member to be raised to a liquid supply position at which said opening of said downward-extending wall of said valve seat member is uncovered from said tubular wall of said valve member; a first conduit for hydraulically communicating said liquid discharge port of said casing body with said lower chamber and having a liquid receipt port projecting into said water discharge port; a second conduit for hydraulically communicating said liquid discharge port of said casing body with said upper chamber and having a liquid receipt port projecting into said liquid discharge port; and a third conduit diverging from said second conduit and extending in the downward direction, the liquid received by said liquid receipt port of said second conduit flowing down through said third conduit until the liquid level has not reached a preset level so that the lower end opening of the third conduit is exposed to the atmosphere and flowing upward through said second conduit for filling said upper chamber when the lower end opening of said third conduit is submerged under the surface of the accumulated liquid.

DESCRIPTION OF THE DRAWING

The single drawing appended hereto is a sectional view showing a preferred embodiment of this invention.

DESCRIPTION OF THE PREFERRED EMBODIMENT

A full understanding of the objects and advantages of the present invention will be had by reading the following detailed description of the invention with reference to the drawing. In the following description, a preferred embodiment of this invention is incorporated in a piping for supplying warm water to a bath tub. However, it should be appreciated that the automatic liquid-supply stopper plug according to this invention is not limited for such a use but may be used in a variety of liquid supply systems, for example, as a nozzle in a piping system for transferring a variety of liquids including petroleum or solutions of chemical substances or as a water plug for saving water consumption.

Referring to the drawing, a preferred embodiment of the automatic liquid-supply stopper plug according to this invention is generally shown by reference numeral 10 and has a casing body 11 of generally hollow cylinder. The casing body 11 comprises an upper casing 12, an intermediate valve casing 14 fluid-tightly connected to the upper casing 12, and a lower casing 15 fluid-tightly connected to the valve casing 14.

The upper casing 12 is generally of cap shape and has a peripheral wall 16 having bored portion to form an inlet port 17. A threaded fitting 20 is mounted around the bore forming the inlet port 17, and an external half of the inner periphery 21 of the bore is threaded so that the screw thread of the fitting 20 continues with the screw thread formed on the inner periphery 21 of the bore. A packing 22 is received in the innermost portion of the threaded portion of the bore. In use, one end of a warm water feed pipe 23 having the other end communicating with a mixing valve (not shown) for mixing cold water with hot water from a hot water source is threaded through the fitting 20 into the screw thread formed on the inner periphery of the bore until the packing 22 is compressed to prevent water leakage.

The upper casing 12 has a top wall 24, and an integral boss 25 projects downward from the center of the lower face of the top wall 24 and has a central bore 26. The inner periphery of the boss 25 defining the central bore has two annular recesses, as shown, for receiving packings 27 and 30 respectively. As will be described in detail hereinafter, an operation rod 74 for pulling-up a valve member 67 projects through the central bore 26 for sliding movement under sealed condition.

The peripheral wall 16 and the top wall 24 of the upper casing 12 defines a top space 31 which serves as a passage for passing warm water from the feed pipe 23.

An expanded skirt portion 32 is provided at the lower end of the peripheral wall 16 of the upper casing 12, and a threaded annular recess 33 is formed around the inner periphery of the expanded skirt portion 32. An end of the valve casing 14 is sealingly threaded into this annular recess 33.

The valve casing 14 is generally of the shape of hollow cylinder and has an upper end 34 which is expanded outward. This outward-expanded end 34 has an upper internal periphery around which an annular recess 35 is formed. An annular flange 40 of an inverted cup shaped member 37, as will be described in detail hereinafter, is seated through a packing 36 on the annular recess 35. Another packing 38 is placed on the annular flange 40 and pressed against the inner face of the annular recess 33 of the expanded skirt portion 32 of the upper casing 12 when the valve casing 14 is threaded to be sealingly connected to the upper casing 12.

As has been described above, the inverted cup shaped member 37 has the annular flange 40 at the upper portion thereof, and the annular flange 40 is provided with a plurality of windows 41 to form passages for passing warm water from the top space 31. The annular flange 40 of the inverted cup shaped member 37 is fixedly clamped by the upper casing 12 and the valve casing 14, so that the main body 42 of the inverted cup shaped member 37 is held centrally of the valve casing 14 under a suspended condition. The main body 42 of the inverted cup shaped member 37 has a slightly expanded lower portion within which a cylindrical chamber 44 is formed centrally thereof and extending in the vertical direction. This cylindrical chamber 44 receives a compression spring 80 and communicates with a conduit for stopping water supply, as will be mentioned hereinafter. The external periphery of the lower portion is provided with an annular groove in which a packing 45 is fitted.

The lower portion of the cylindrical body 46 of the valve casing 14 defines an integral flange 47, and a plurality of bolt holes is provided at the periphery of the flange 47. On the other hand, the upper portion of the lower casing 15 defines a flange 47 having the diameter same as that of the flange 47, and a plurality of bolt holes is provided at the positions corresponding to the bolt holes of the flange 47. An annular recess 51 is formed at the center of the flange 50. A valve seat member 52, which will be described in detail hereinafter, is seated on the annular recess 51 of the flange 50, and the flange 47 of the valve casing 14 and the flange 50 of the lower casing 15 are fluid-tightly connected through an O-ring 53 and a packing 54 by a plurality of bolts 55 one of which is shown in the right side of the drawing.

The valve seat member 52 is generally of an inverted cup shape and has an integral flange 56 which is clamped between the valve casing 14 and the lower casing 15, as described hereinbefore. A plurality of openings 60 is provided on the peripheral wall of the main body 57 of the valve seat member 52, and also provided at the upper position of the peripheral wall of the main body 57 is an annular groove in which an annular packing 61 is mounted. A first conduit 81 for holding the valve member 67 at the raised position, as will be described in detail hereinafter, projects through the top wall 62 of the valve seat member 52. A chamber 63 is defined within the valve seat member 52 and serves as a passage for the liquid flowing through the openings 60 when the valve member 67 is opened to uncover the opening 60.

An annular groove 64 is formed on the upper face of the flange 56 of the valve seat member 52. The annular groove 64 has a stepped section, and an O-ring 66 is fitted in the inner stepped portion of the groove 64. The O-ring 66 serves as the valve seat for the valve member 67, as will be described in detail hereinafter.

The vertical section of the valve member 67 has a shape of letter H, and the valve member 67 comprises a tubular wall 70 and a partition wall 71 for dividing the tubular space defined by the wall 70 into two sections. The upper portion of the tubular wall 70 and the upper face of the partition wall 71 defines an upper chamber 72, and the lower portion of the tubular wall 70 and the lower face of the partition wall 71 defines a lower chamber 73. The lower portion of the tubular wall 70 surrounds the main body 57 of the valve seat member 52 and fluid-tightly engaged with the packing 61, so that the valve member 67 slides in the vertical direction while engaging fluid-tightly against the main body 57 of the valve seat member 52. Similarly, the upper portion of the tubular wall 70 surrounds the lower portion 43 of the inverted cup shaped member 37 and fluid-tightly engaged with the packing 45, so that the valve member 67 slides in the vertical direction while engaging fluid-tightly against the lower portion 43 of the inverted cup shaped member 37.

The top end portion of the tubular wall 70 of the valve member 67 is fixedly connected to an operation rod 74 which projects through the boss 25 of the upper casing 12, as described hereinbefore. A knob 75 is mounted on the upper end of the operation rod 74, and the valve member 67 may be raised upward to open the openings 60 of the valve seat member 52 by pulling up the knob 75 manually.

An annular chamber 76 is defined by the valve casing 14, the inverted cup shaped member 37 and the valve member 67 for allowing warm water to flow therethrough. A stud 77 is integrally formed on the upper face of the partition wall 71 of the valve member 67, and one end of a compression spring 80 surrounds the stud 77 and the other end of the spring 80 abuts against the ceiling face of the cylindrical chamber 44 formed within the inverted cup shaped member 37 to depress the valve member 67 in the downward direction. The stud 77 is provided to limit the transverse movement of the spring 80.

A first conduit 81 for supplying the water pressure for holding the valve member 67 at the open position and a second conduit 82 for supplying the water pressure for moving the valve member 67 to the close position are disposed within the lower casing 15. The lower casing 15 has a hollow central portion which serves as a discharge port for warm water.

The first conduit 81 has a liquid receipt port 83 from which warm water flows upward through the first conduit 81 onto the lower chamber 73 of the valve member 67. On the other hand, the second conduit 82 has a liquid receipt port 84 from which warm water flows upward through the conduit 82 to the cylindrical chamber 44 defined by the inverted cup shaped member 37 and then onto the upper chamber 72 of the valve member 67. However, a water level detection conduit or third conduit 85 diverges from the second conduit 82 so that warm water received by the liquid receipt port 84 flows through the third conduit 85 and does not flow upward through the second conduit 82 until the lower end opening of the water level detection conduit is submerged into the accumulated warm water and the water flow through the conduit 85 is prevented. After the end opening of the water level detection conduit 85 is submerged into the accumulated warm water, the warm water received by the liquid receipt port 84 flows upward through the second conduit 82.

The operation of the automatic liquid-supply stopper plug according to this invention will now be described. The embodiment shown in the appended drawing is at the position when the liquid level reaches a preset level $L_1$ and the valve member 67 covers the openings 60 of the valve seat member 52. Under this condition, water supply from the warm water source is stopped automatically.

Supposing now that the water level in the bath tub is at the level $L_2$ and it is desired to charge warm water in the bath tub until the water level reaches $L_1$, the operator may simply pull up the knob 75 against the action of the compression spring 80. When the knob 75 is pulled up, the valve member 67 is raised by the operation rod 74 so that the openings 60 of the valve seat member 52 are uncovered from the valve member 67 to be opened. As the result, the chamber 63 defined by the valve seat member 52 communicates with the annular chamber 76 through the openings 60. Simultaneously, the lower chamber 73 of the valve member 67 is extended until the upper face of the partition wall 71 of the valve member 67 abuts against the lower end 43 of the inverted cup shaped member 37 at the most. In other words, the sectional area of the lower chamber 73 may be extended to have the area substantially equal to that of the upper chamber 72 under the condition as illustrated in the drawing when the knob is pulled up to the uppermost position, while the volume of the upper chamber 72 is decreased correspondingly.

Under this open condition, warm water supplied from a mixing valve (not shown) of a water supply source flows through the water feed pipe 23 and through the inlet port 17, and then flows in the top space 31 of the upper casing 12 and passes through the annular chamber 76, as shown by the arrow A, and through the openings 60, the chamber 63 and the liquid discharge port 63 to be poured into the bath tub.

Portions of the warm water flowing from the chamber 63 are received by the liquid receipt ports 83 and 84 of the first and second conduits 81 and 82 projecting into the liquid discharge port 86 within the lower casing 15. The warm water received by the liquid receipt port 83 of the first conduit 81 flows upward, as shown by the arrow B, by the action of water pressure into the lower chamber 73 of the valve member 67 to fill the lower chamber 73 having the enlarged volume by being raised as mentioned above. The warm water filling in the lower chamber 73 acts to press the partition wall 71 of the valve member 67 upward. Because the compression force of the spring 80 is set to be lower than the water pressure acting on the face of the partition wall 71, the valve member 67 is held at the raised position even if the operator releases the knob 75.

On the other hand, the warm water received by the liquid receipt port 84 of the second conduit 82 flows through the line denoted by the arrow D to pass through the water level detection conduit 85 to be poured into the bath tub, since the lower end opening of the water level detection conduit 85 is not yet submerged into the warm water accumulated in the bath tub. Under this condition, the warm water received by the liquid receipt port 84 does not flow upward through the second conduit 82.

Warm water is fed through the automatic water-supply stopper plug 10 of the invention having the valve member held at the raised position to the bath tub until the liquid level of warm water accumulated in the bath tub arrives at the level $L_1$ to which level the lower end of the water level detection conduit 85 extends. When the water level arrives at the level $L_1$ and the lower end of the conduit 85 is submerged into the warm water accumulated in the bath tub, the flow line of warm water through the conduit 85 is blocked so that the warm water received by the liquid receipt port 84 flows upward through the conduit 82, as shown by the arrow C into the upper chamber 72 of the valve member 67 through the cylindrical chamber 44 in the inverted cup shaped member 37.

The warm water flowing into the upper chamber 72 acts on the upper face of the partition wall 71 to depress the valve member 67. Since the area of upper face of the partition wall 71 is substantially equal to the area of lower face of the partition wall 71, the water pressure by the warm water filling in the upper chamber 72 and that applied by the warm water in the lower chamber 73 is cancelled each other, and as a result the effective force applied on the valve member 67 becomes equal to the depression force acted by the compression spring 80.

Accordingly, the valve member 67 is depressed by the action of the spring 80 so that the warm water filling in the lower chamber is discharged through the first conduit 81. However, since the diameter of the conduit 81 is relatively small, the discharge of water from the lower chamber is highly resisted so that the valve member 67 is lowered slowly at a low speed. Due to this damping action, the lowering valve member 67 closes the openings 60 of the valve seat member 52 gradually by the slack motion.

As an advantageous effect of such a gradual and slack closing movement of the valve member 67, the water hammering action inevitable by the use of a conventional water-supply stopper plug involving a mechanism of instantaneous closing of the valve member can be avoided. It has been empirically ascertained that substantially no water-hammering occurs in the automatic water-supply stopper valve manufactured in accordance with the present invention.

As will be apparent from the foregoing, according to the present invention, water supply is automatically stopped by cancelling the water pressure applied on the lower face of the partition wall 71 by the water pressure applied on the upper face of the partition wall 71 by the filling water supplied through the conduit 82 into the upper chamber 72. In other words, water supply is automatically stopped independently of the volume of warm water to be accumulated in the bath tub. Accordingly, the volume or level of warm water to be accumulated in the bath tub may be adjusted, as desired, simply by raising or lowering the lower end of the water level detection conduit 85 by any suitable means.

Although the present invention has been described by referring to a preferred embodiment thereof, it should be appreciated that the present invention is not limited only to the illustrated embodiment but many modifications and changes will be made by those skilled in the art without departing from the broad scope and spirit of this invention. It is intended to embrace all such modifications and changes within the scope of the invention as defined in the appended claims. For example, the valve member 67 may be fluid-tightly connected to the inverted cup shaped member 37 by means of bellows.

The embodiment wherein the valve member 67 is fluid-tightly connected to the inverted cup shaped member 37 by bellows is particularly suited for use in the water-supply system for public service in combination with an appropriate water charge equipment. In detail, in the water supply system for public service, it is necessary to provide a device for preventing the backward flow of water, such as a breaker, at a position considered to be particularly requisite for preventing contamination of backward flow even when a negative pressure is generated at the water source to cause the risk of backward flow to the water supply side resulting in contamination of supply water. Since the valve member and the inverted cup shaped member are fluid-tightly connected with one another by bellows, and hence the use of packing 45 subjected to abrasion to cause leakage of water is avoided in this modification, the water once discharged through the liquid discharge port 86 is so completely shut out from the water supply side of the plug. Accordingly, contamination of water by the once discharged water is completely prevented without the need of a braker or other like devices.

The liquid receipt ports of the conduits 81 and 82 may be provided in the lower portion of the valve seat member 52. The liquid level detection conduit may be provided with any means for adjusting the height or length thereof, or otherwise may be interchangeably fitted at an intermediate position of the second conduit 82.

What is claimed is:

1. An automatic liquid-supply stopper plug, comprising:
   a casing body 11 having an inlet port 17 at the upper portion thereof and a liquid discharge port 86 at the lower end portion thereof;
   an inverted cup shaped member 37 fixedly received in said casing body 11 to be suspended within said casing body 11;
   a valve seat member 52 mounted in said casing body at the position below said inverted cup shaped member 37 and having a generally tubular wall 57 extending downward from the top face thereof, said downward-extending wall 57 being provided with at least one window type opening 60 communicating with said liquid discharge port 86 of said casing body 11;
   a movable valve member 67 having a generally tubular wall 70 and a partition wall 71 of disk shape for sealingly and slidably surrounding said inverted cup shaped member 37 and for sealingly and disengageably covering said window type opening 60 of said valve seat member 52 to open or close said opening 60, said tubular wall 70 and said partition wall 71 defining an upper chamber 72 in combination with said inverted cup shaped member 37, and said tubular wall 70 and said partition wall 71 defining a lower chamber 73 in combination with said valve seat member 52;
   a compression spring 80 fitted between the inner face of said inverted cup shaped member 37 and the top face of said valve member 67 for normally depressing said valve member 67 in the downward direction;
   a manually operated knob 75 connected to said valve member 67 to be raised to a liquid supply position at which said opening 60 of said downward-extending wall of said valve seat member 52 is uncovered from said tubular wall 70 of said valve member 67;
   a first conduit 81 for hydraulically communicating said liquid discharge port 86 of said casing body 11 with said lower chamber 73 and having a liquid receipt port 83 projecting into said liquid discharge port 86;
   a second conduit 82 for hydraulically communicating said liquid discharge port 86 of said casing body 11 with said upper chamber 72 and having a liquid receipt port 84 projecting into said liquid discharge port 86; and
   a third conduit 85 diverging from said second conduit 82 and extending downward to detect the liquid level, the liquid received by said liquid receipt port 84 flowing down through said third conduit until the liquid level has not reached a pre-set level so that the lower end opening of said third conduit 85 is exposed to atmosphere and flowing upward through said second conduit 82 for filling into said upper chamber 72 when the lower end opening of said third conduit 85 is submerged under the surface of the accumulated liquid.

2. The automatic liquid-supply stopper plug as claimed in claim 1, wherein said casing body 11 comprises a generally cap shaped under casing 12, a generally hollow cylindrical valve casing 14 sealingly connected to said upper casing, and a generally hollow cylindrical lower casing 15 sealingly connected to said valve casing 14.

3. The automatic liquid-supply stopper plug as claimed in claim 2, wherein said upper casing 12 has a peripheral wall 16 formed with said inlet port 17, and said inlet port 17 is provided with means for snugly coupling an end of a pipe communicating with a liquid source.

4. The automatic liquid-supply stopper plug as claimed in claim 2, wherein said upper casing 12 has a top plate 24 provided with an integrally molded boss 25 extending downward and having a center hole 26 through which an operation rod 74 projects upward to carry said manually operated knob 75 and extends downward to be connected to said valve member 67.

5. The automatic liquid-supply stopper plug as claimed in claim 1, wherein said inverted cup shaped member 37 comprises an annular flange 40 and a main body 42 integrally connected to said annular flange and extending in the downward direction.

6. The automatic liquid-supply stopper plug as claimed in claim 5, wherein said annular flange 40 has an edge portion to be clamped between said upper casing 12 and said valve casing 11 and also has a plurality of openings 41 for allowing the passage of water or other liquids therethrough.

7. The automatic liquid-supply stopper plug as claimed in claim 5, wherein said main body 42 has said generally tubular wall 43 forming a generally cylindrical cavity 44 for receiving said compression spring 80, and wherein a peripheral groove for receiving a packing 45 securing a liquid-tight engagement with the inner face of said peripheral wall 70 is formed around the peripheral face of said generally cylindrical wall 43.

8. The automatic liquid-supply stopper plug as claimed in claim 1, wherein said valve seat member 52 is generally of the shape of inverted cup and has a flange 56 at the lower portion thereof and a main body 57 integral with said flange 56.

9. The automatic liquid-supply stopper plug as claimed in claim 8, wherein said main body 57 includes said downward-extending wall 57 on which a plurality of said openings 60 are provided to be opened or closed by said valve member 67.

10. The automatic liquid-supply stopper plug as claimed in claim 8, wherein an annular groove 64 for receiving the lower end of said tubular wall 70 of said valve member 67 is provided on the upper face of said flange 56 of said valve seat member 52.

11. The automatic liquid-supply stopper plug as claimed in claim 1, wherein said valve casing 14 has a flange 47 at the lower portion thereof and said lower casing 15 has a flange 50 at the upper portion thereof, the upper face of said flange 50 being provided with an annular recess 51 in which said flange 56 said valve seat member 52 is received to be clamped between said flange 47 and said flange 50 so that said valve seat member is fixedly contained within said casing body 11.

12. The automatic liquid-supply stopper plug as claimed in claim 1, wherein a stud 77 for limiting the horizontal movement of said spring 80 is integrally formed on and projecting upward from the upper face of said partition wall 71 of said valve member 67.

13. The automatic liquid-supply stopper plug as claimed in claim 1, wherein a portion of said first conduit 81 passes through the peripheral wall of said lower casing 15.

14. The automatic liquid-supply stopper plug as claimed in claim 1, wherein a portion of said second conduit 82 passes through the peripheral wall of said lower casing 15.

15. The automatic liquid-supply stopper plug as claimed in claim 1, wherein said inverted cup shaped member 37 comprises an annular flange 40 and bellows depending downward from said annular flange, the lower peripheral edge of said bellows being connected to the upper peripheral edge of said valve member 67.

* * * * *